(12) United States Patent
Skulachev et al.

(10) Patent No.: US 9,408,859 B2
(45) Date of Patent: *Aug. 9, 2016

(54) PHARMACEUTICAL COMPOSITIONS USEFUL FOR PREVENTING AND TREATING CANCER

(71) Applicant: Mitotech SA, Luxembourg (LU)

(72) Inventors: Vladimir P. Skulachev, Moscow (RU); Maxim V. Skulachev, Moscow (RU)

(73) Assignee: MITOTECH S.A., Luxembourg (LU)

( * ) Notice: Subject to any disclaimer, the term of this patent is extended or adjusted under 35 U.S.C. 154(b) by 0 days.

This patent is subject to a terminal disclaimer.

(21) Appl. No.: 13/674,443

(22) Filed: Nov. 12, 2012

(65) Prior Publication Data

US 2013/0072463 A1 Mar. 21, 2013

Related U.S. Application Data

(63) Continuation-in-part of application No. 12/524,961, filed as application No. PCT/RU2007/000044 on Jan. 29, 2007, now Pat. No. 8,349,902.

(51) Int. Cl.

| | |
|---|---|
| *A61K 31/66* | (2006.01) |
| *A61K 31/4745* | (2006.01) |
| *A61K 31/352* | (2006.01) |
| *A61K 31/4355* | (2006.01) |
| *A61K 31/473* | (2006.01) |
| *A61K 31/4741* | (2006.01) |

(52) U.S. Cl.
CPC .............. *A61K 31/66* (2013.01); *A61K 31/352* (2013.01); *A61K 31/4355* (2013.01); *A61K 31/473* (2013.01); *A61K 31/4741* (2013.01); *A61K 31/4745* (2013.01)

(58) Field of Classification Search
None
See application file for complete search history.

(56) References Cited

U.S. PATENT DOCUMENTS

| | | | |
|---|---|---|---|
| 5,538,974 | A | 7/1996 | Ogawa et al. |
| 6,331,532 | B1 | 12/2001 | Murphy et al. |
| 7,109,189 | B2 | 9/2006 | Murphy et al. |
| 2002/0044913 | A1 | 4/2002 | Hamilton |
| 2007/0270381 | A1 | 11/2007 | Murphy et al. |
| 2008/0275005 | A1 | 11/2008 | Murphy et al. |

FOREIGN PATENT DOCUMENTS

| | | |
|---|---|---|
| EP | 1047701 B1 | 5/2005 |
| EP | 1534720 A1 | 6/2005 |
| EP | 1321138 B1 | 4/2006 |
| RU | 2318500 C2 | 3/2008 |
| WO | 99/26582 A2 | 6/1999 |
| WO | 2004/014927 A1 | 2/2004 |
| WO | 2006/005759 A2 | 1/2006 |
| WO | 2007/046729 A1 | 4/2007 |
| WO | 2008/048134 A1 | 4/2008 |
| WO | 2009/005386 A1 | 1/2009 |
| WO | WO 2011108946 A1 * | 9/2011 |

OTHER PUBLICATIONS

Bakeeva et al. Biochemistry (Moscow), 2008, vol. 73, No. 12, pp. 1288-1299.*
Agapova, et al. (2008) "Mitochondria-Targeted Plastoquinone Derivatives as Tools to Interrupt Execution of the Aging Program. 3. Inhibitory Effect of SkQ1 on Tumor Development From p53-Deficient Cells," Biochem. (Mosc)., 73(12):1300-1316 (+ 3 fig. pages).
Antonenko, et al. (2008) "Mitochondria-Targeted Plastoquinone Derivatives as Tools to Interrupt Execution of the Aging Program. 1. Cationic Plastoquinone Derivatives: Synthesis and In Vitro Studies," Biochem. (Mosc)., 73(12):1273-1287 (+ 1 fig. page).
Dugina, et al. (2009) "β- and γ-Cyoplasmic Actins Display Distinct Distribution and Functional Diversity," J. Cell Sci., 122(16):2980-2988.
Fernández-Medarde, et al. (2011) "Ras in Cancer and Developmental Diseases," Genes & Canc., 2(3):344-358.
Havens, et al. (2006) "Regulation of Late G1/S Phase Transition and APCCdh1 by Reactive Oxygen Species," Mol. Cell. Biol., 26(12):4701-4711.
Popova, et al., (2010) "Scavenging of Reactive Oxygen Species in Mitochondria Induces Myofibroblast Differentiation," Antiox. & Redox. Signal., 13(9):1297-1307.
Pylayeva-Gupta, et al. (2011) "RAS Oncogenes: Weaving a Tumorigenic Web," Nature Reviews/Canc., 11:761-774.
Sundaresan, et al. (1995) "Requirement for Generation of H2O2 for Platelet-Derived Growth Factor Signal Transduction," Science, 270:296-299.
Adlam et al. (2005) "Targeting an antioxidant to mitochondria decreases cardiac ischemia-reperfusion injury," FASEB J., 19:1088-1095.
Anisimov (2007) "Molecular and Physiological Mechanisms of Aging," Antioksidanty, Nov. 27, 2007, [on line] http://imquest.alfaspace.net/Book/MFMA/mfma_3_9_2.htm?embedded=yes translated from Russian to English.
Antonenko et al. (2008) "Protective effects of mitochondria-targeted antioxidant SkQ in aqueous and lipid membrane environments," J. Membr. Biol., 222:141-149.
Becker (2004) "New concepts in reactive oxygen species and cardiovascular reperfusion physiology" Cardiovascular Research, 61:461-470.

(Continued)

*Primary Examiner* — Jeffrey S Lundgren
*Assistant Examiner* — Stephanie Springer
(74) *Attorney, Agent, or Firm* — Wayne A. Keown; Verrill Dana LLP

(57) ABSTRACT

Disclosed is a method of treating a cancer on a mammal, comprising administering to the mammal in need thereof a therapeutically effective amount of a compound

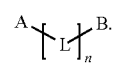

18 Claims, 9 Drawing Sheets
(1 of 9 Drawing Sheet(s) Filed in Color)

(56) References Cited

OTHER PUBLICATIONS

Berge et al. (1977) "Pharmaceutical Salts," J. Pharma. Sci., 66(1):1-19.
Blaikie et al. (2006) "Targeting Dinitrophenol to Mitochondria: Limitations to the Development of a Self-limiting Mitochondrial Protonophore," Biosci. Rep, 26:231-243.
Brand et al. (1992) "The mechanism of the increase in mitochondrial proton permeability induced by thyroid hormones," Eur. J. Biochem. 206:775-781.
Doughan et al. (2007) "Original Research Communication: Mitochondrial Redox Cycling of Mitoquinone Leads to superoxide Production and Cellular Apoptosis," Antioxid. & Redox Signal., 9(11):1825-1836.
Emiko et al. (2005) "Manganese Superoxide Dismutase protects against oxidation-induced apoptosis in mouse retinal pigment epithelium: implications for age-related macular degeneration," Invest. Ophthalmol. Vis. Sci., 46(9):3426-3434.
Green et al. (2004) "Prevention of Mitochondrial Oxidative Damage as a Therapeutic Strategy in Diabetes," Diabetes, 53(1):S110-S118.
Hansford et al. (1997) "Dependence of H2O2 formation by rat heart mitochondria on substrate availability and donor age," J. Bioenerg. Biomem. 29(1):89-95.
Holloszy (1998) "Longevity of exercising male rats: effect of an antioxidant supplemented diet," Mechanisms of Ageing and Development, 100:211-219.
King et al. (2004) "Mitochondria-derived reactive oxygen species mediate blue light-induced death of retinal pigment epithelial cells," Photochem. and Photobiol, 79(5):470-475.
Kirschner et al. (1994) "Role of iron and oxygen-derived free radicals in ischemia-reperfusion injury" J. Am. Coll. Surg., 179:103-117.
Li et al. (2000) "Skeletal muscle respiratory uncoupling prevents diet-induced obesity and insulin resistance in mice," Nat. Med. 6(10):1115-1120.
Liu et al. (1993) "Age-associated changes in superoxide dismutase activity, thiobarbituric acid reactivity and reduced glutathione level in the brain and liver in senescence accelerated mice (SAM): a comparison with ddY mice," Mech. Ageing & Dev., 71:23-30.
Longo et al. (2005) "Programmed and altruistic ageing," Nature Reviews Genetics, 6:866-872.
Lou et al. (2007) "Mitochondrial Uncouplers With an Extraordinary Dynamic Range," Biochem. J., 407:129-140.
Mecocci et al. (2000) "Plasma antioxidants and longevity: a study on healthy centenarians," Free Radical Biology and Medicine, 28(8):1243-1248.
Neroev et al. (2008) Mitochondria-Targeted Plastoquinone Derivatives as Tools to Interrupt Execution of the Aging Program. 4. Age-Related Eye Disease. SkQ1 Returns Vision to Blind Animals, Biochemistry (Mosc.), 73 (12):1317-1328.
Orr et al. (2003) "Effects of overexpression of copper—zinc and manganese superoxide dismutases, catalase, and thioredoxin reductase genes on longevity in *Drosophila melanogaster*," J. Biol. Chem., 278(29):26418-26422.
Papp et al. (1999) "Glutathione status in retinopathy of prematurity," Free Radic. Biol. & Med., 27(7-8):738-743.
Petrosillo et al. (2005) "Mitochondrial dysfunction associated with cardiac ischemia/reperfusion can be attenuated by oxygen tension control. Role of oxygen-free radicals and cardiolipin," Biochimica et Biophysica Acta, 1710:78-86.
Petrosillo et al. (2006) "Protective effect of melatonin against mitochondrial dysfunction associated with cardiac ischemia-reperfusion: role of cardiolipin," FASEB J., 20:269-276.
Popova et al. (2006) "MitoQ induced miofibroblast differentiation of human fibroblasts," Biochimica et Biophysica Acta, S:433-434.
Pozniakovsky et al. (2005) "Role of mitochondria in the pheromone- and amiodarone-induced programmed death of yeast," J. Cell Biol., 168(2):257-69.
Reddy (2006) "Mitochondrial oxidative damage in aging and Alzheimer's disease: implications for mitochondrially targeted antioxidant therapeutics," J. Biomedicine and Biotech., Art. ID31372:1-13.
Reliene et al. (2007) "Antioxidants suppress lymphoma and increase longevity in the atm-deficient mice," J. Nutrition, 37:229S-232S.
Riess et al. (2004) "Reduced reactive O2 species formation and preserved mitochondrial NADH and [Ca2+] levels during short-term 17° C ischemia in intact hearts," Cardiovascular Research, 61:580-590.
Skulachev (2007) "A Biochemical Approach to the Problem of Aging: 'Megaproject' on Membrane-Penetrating Ions. The First Results and Prospects," Biochem. (Moscow), 72(12):1385-1396.
Sheu et al. (2006) "Targeting antioxidants to mitochondria: a new therapeutic direction," Biochimica et Biophysica Acta, 1762:256-265.
Sidorova et al. (2004) "Transcriptional activation of cytochrome P450 1A1 with alpha-tocopherol," Bull Exp. Bio. Med., 138(3):233-236.
Skulachev (2005) "Critical Review: How to Clean the Dirtiest Place in the Cell: Cationic Antioxidants as Intramitochondrial ROS Scavengers," IUBMB Life, 57(4/5):305-310.
Skulachev (2003) "Aging and the programmed death phenomena," Topics in Current Genetics, vol. 3, Nystrom and Osiewacz, Eds., Model systems in Aging, Springer-Verlag Berlin Heidelberg 191-238.
Starkov et al. (1997) "6-ketocholestanol is a recoupler for mitochondria, chromatophores and cytochrome oxidase proteoliposomes," Biochim. Biophys. Acta. 1318:159-172.
Tompkins et al. (2006) "Mitochondrial dysfunction in cardiac ischemia-reperfusion injury: ROS from complex I, without inhibition," Biochim Biophys Acta 1762:223-231.
Yildirim et al. (2005) "Role of oxidative stress enzymes in open-angle glaucoma," Eye, 19:580-583.
Zweier et al. (1987) "Direct measurement of free radical generation following reperfusion of ischemic myocardium," PNAS USA, 84:1404-1407.
International Search Report dated Dec. 20, 2007 and International Preliminary Report on Patentability dated Nov. 10, 2009, PCT/RU2007/000171 (16 pages).
International Search Report and Written Opinion of the International Searching Authority, PCT/RU2007/000355, Mar. 27, 2008, 10 pages.
PCT International Preliminary Report on Patentability for International Application No. PCT/RU2007/000043, issued Aug. 4, 2009, 7 pages.
PCT International Search Report for PCT Application No. PCT/RU2007/000043, mailed Nov. 1, 2007, 2 pages.
PCT International Search Report and Written Opinion of the International Searching Authority for PCT Application No. PCT/RU2006/000546, mailed Jul. 5, 2007, 14 pages.
International Search Report, PCT/RU2008/000706, Aug. 13, 2009 (3 pages).
International Search Report and Written Opinion of the International Searching Authority, PCT/RU2009/000295, Feb. 25, 2010, 7 pages.
International Search Report and Written Opinion, PCT/RU2009/000621, dated Aug. 12, 2010 (12 pages).
International Search Report and Written Opinion, PCT/RU2006/000394, dated Nov. 2, 2006 (6 pages).
International Search Report and Written Opinion, PCT/RU2006/000547, dated Jul. 5, 2007 (7 pages).
International Search Report and Written Opinion, PCT/RU2007/000044, dated Nov. 1, 2007 (9 pages).
Zorov et al. (2006), Mitochondrial ROS-induced ROS release: an update and review, Biochim. Biophys. Acta. 1757:509-517.
13-Methoxydihydronitidine—Compound Summary PubChem compound CID 38845; Mar. 26, 2005 [retrieved_from http://pubchem.ncbi.nlm.nih.gov/summary/summary.cgi?cid=38845&loc=ec_rcs on Jul. 31, 2012] whole doc (4 pages).
Bacsi et al. (2005) "Effect of pollen-mediated oxidative stress on immediate hypersensitivity reactions and late-phase inflammation in allergic conjuctivitis," J. Allergy Clin Immunol., 116(4): 836-843.
Barclay et al. (2003) Phenols as antioxidants. In the Chemistry of Phenols, Part 2, Rappoport, Z., Ed., Wiley, pp. 875 (3 pages).
Cherubini et al. (2005). Potential markers of oxidative stress in stroke. Free Radic Biol Med 39, 841-852.
Coulter et al. (2000) "Mitochondrially targeted antioxidants and thiol reagents," Free Rad. Biol. Med. 28 (10):1547-1554.

(56) References Cited

OTHER PUBLICATIONS

Denisov (2006) "Reactivity of quinones as alkyl radical acceptors," Kinetics and Catalysis, 45(5):662-671.
Dominguez (2006), "Ageing, lifestyle modifications, and cardiovascular disease in developing countries," J. Nutr. Health Aging, 10(2):143-149.
Galkina et al. (2004). "Endothelium-leukocyte interactions under the influence of the superoxide-nitrogen monoxide system." Med. Sci. Monit. 10:BR307-316.
Gear (1974) "Rhodamine 6G: A potent inhibitor of mitochondrial oxidative phosphorylation," J. Biol. Chem., 249 (11):3628-3637.
Giamarellos-Bourboulis et al. (2006). "Oleuropein: a novel immunomodulator conferring prolonged survival in experimental sepsis by Pseudomonas aeruginosa." Shock 26(14):410-416.
Giorgini et al. (2001) "Reactivity of ubiquinones and ubiquinols with free radicals." Free Rad. Res. 35:63-72.
Goldstein (2002) "Reactive oxygen species as essential components of ambient air," Biochemistry (Mosc.) 67:161-170.
Griffiths et al. (2001) "Genetic analysis of collagen-induced arthritis in rats: a polygenic model for rheumatoid arthritis predicts a common framework of cross-species inflammatory/autoimmune disease loci." Immunol. Rev. 184:172-83.
Haass et al. (2007) "Soluble protein oligomers in neurodegeneration: lessons from the Alzheimer's amyloid beta-peptide." Nat. Rev. Mol. Cell. Biol. 8:101-112.
Hummel et al. (1966) "Diabetes, new mutation in the mouse." Science, 153:1127-1128.
Hunter et al. (1979). "The Ca2+-induced membrane transition in mitochondria. I. The protective mechanisms." Arch. Biochem. Biophys. 195:453-459.
Johnson et al. (1980) "Localization of Mitochondria in Living Cells with Rhodamine 123," Proc. Natl. Acad. Sci. USA, 77(2):990-994.
Jolkkonen (2000) "Behavioral effects of the alpha(2)-adrenoceptor antagonist, atipamezole, after focal cerebral ischemia in rats," Eur. J. Pharmacol., 400, 211-219.
Juhaszova et al. (2004). "Glycogen synthase kinase-3beta mediates convergence of protection signaling to inhibit the mitochondrial permeability transition pore." J. Clin. Invest. 113:1535-1549.
Karl et al. (2003) "Behavioral phenotyping of mice in pharmacological and toxicological research," Exp. Toxicol. Pathol., 55(1):69-83.
Kirkinezos et al (2001) "Reactive Oxygen species and Mitochondrial Diseases," Seminars in Cell & Developmental Biology, 12:449-457.
Kroemer et al. (1995). "The biochemistry of programmed cell death" FASEB J. 9:1277-1287.
Li et al. (2002). "Activation of macrophage nuclear factor-kappa B and induction of inducible nitric oxide synthase by LPS." Respir. Res. 3:23 (6 pages).
Liu et al. (1996). "Induction of apoptotic program in cell-free extracts: requirement for dATP and cytochrome c." Cell 86:147-157.
Lysenko et al. (2001) "Thrombocytopathies and their role in the development of hemorrhagic syndrome in vascular diseases of the fundus oculi," Vestn. Oftalmol., 117(1):24-26 (English Translation of Russian article abstract—1 page).
Maire et al. (2001) "Factors associated with hyperhomocysteinemia in Crohn's disease," Gastroenterol. Clin. Biol., 25(8-9):745-748 (French-abstract only, 1 page).
Malenka et al. (1999) "Long-term potentiation: a decade of progress?" Science, 285(5435):1870-1874.
Matsumoto et al. (1992). "Antioxidant effect on renal scarring following infection of mannose-sensitive-piliated bacteria." Nephron. 60:210-215.
Monaco et al. (2004) "Canonical pathway of nuclear factor kB activation selectively regulates proinflammatory and prothrombotic responses in human atherosclerosis," PNAS, 101(15):5634-5639.
Mundi et al. (1991). "Extracellular release of reactive oxygen species from human neutrophils upon interaction with *Escherichia coli* strains causing renal scarring." Infect. Immun. 59(11):4168-4172.
Murphy et al. (2011) "Homocysteine in pregnancy," Adv. Clin. Chem., 53:105-37.
O'Hanley et al. (1996). "Prospects for urinary tract infection vaccines. In: Urinary Tract Infections: Molecular Pathogenesis and Clinical Management" (Mobley, H. L. T. & Warren, J.W., eds), (Washington, DC: ASM Press), pp. 405-425 (23 pages).
O'Hanley et al. (1991). "Alpha-hemolysin contributes to the pathogenicity of piliated digalactoside-binding *Escherichia coli* in the kidney: efficacy of an alpha-hemolysin vaccine in preventing renal injury in the BALB/c mouse model of pyelonephritis." Infect. Immun. 59(3):1153-1161.
Okada et al. (2005) "The implications of the upregulation of ICAM-1/VCAM-1 expression of corneal fibroblasts on the pathogenesis of allergic keratopathy," Invest. Ophthalmol. Vis. Sci., 46(12):4512-4518.
Petit-Demouliere et al. (2005) "Forced swimming test in mice: a review of antidepressant activity," Psychopharmacol., 177:245-255.
Rodriguez-Spong et al. (2004) "General Principles of Pharmaceutical Solid Polymorphism: A Supramolecular Perspective," Advanced Drug Delivery Reviews, 56:241-274.
Saifer et al. (1957) "Laboratory Methods: The photometric microdetermination of blood glucose with glucose oxidase," J. Lab. Clin. Med., 51(3):448-460.
Sanmun et al. (2009) "Involvement of a functional NADPH oxidase in neutrophils and macrophages during programmed cell clearance: implications for chronic granulomatous disease," Am. J. Physiol. Cell Physiol. 297:C621-631.
Sarter (2002) Coenzyme Q10 and Cardiovascular Disease: A Review, J. Cardiovasc. Nurs. 16(4):9-20.
Selkoe (2002) "Alzheimer's disease is a synaptic failure," Science 298:789-791.
Smith, et al. (2003) "Delivery of bioactive molecules to mitochondria in vivo," PNAS, 100(9):5407-5412.
Spector (1995) "Oxidative stress-induced cataract: mechanism of action," FASEB J., 9:1173-1182.
Stella et al. (2007) Prodrugs: Challenges and Rewards, Springer, New York Part 1 and 2 (17 pages).
USDH (2005) "Guidance for Industry: Estimating the Maximum Safe Starting Dose in Initial Clinical Trials for Therapeutics in Adult Healthy Volunteers," U.S. Dept. of Health and Human Services, FDA, CDER (30 pages).
Viana et al. (2004) "Hypoglycemic and anti-lipemic effects of the aqueous extract from Cissus sicyoides," BMC Pharmacol. 4:9 (7 pages).
Villa et al. (2004) "Animal models of endotoxic shock" Meth. Mol. Med., 98:199-206.
Vollset et al. (2000) "Plasma total homocysteine, pregnancy complications, and adverse pregnancy outcomes: the Hordaland Homocysteine study," Am. J. Clin. Nutr., 71:962-968.
Zamzami et al. (1996), "Mitochondrial control of nuclear apoptosis," J. Exp. Med. 183:1533-1544.
Zoratti et al. (1995), "The mitochondrial permeability transition," Biochim. Biophys. Acta. 1241:139-176.
Zorov et al. (2000), "Reactive oxygen species (ROS)-induced ROS release: a new phenomenon accompanying induction of the mitochondrial permeability transition in cardiac myocytes," J. Exp. Med. 192(7):1001-1014.

* cited by examiner control

Ras-transformed cells

Cells reincubated with SkQ1

Ras-transformed cells reincubated with SkQ1

Control

SkQ1

PHARMACEUTICAL COMPOSITIONS USEFUL FOR PREVENTING AND TREATING CANCER

REFERENCE TO RELATED APPLICATIONS

This application is a continuation-in-part of U.S. patent application Ser. No. 12/524,961, entitled "PHARMACEUTICAL COMPOSITIONS USEFUL FOR PREVENTING AND TREATING ONCOLOGICAL DISEASES," filed on Feb. 16, 2010, which is a National Phase filing of International Patent Application No. PCT/RU2007/000044, filed on Jan. 29, 2007. The entirety of the aforementioned applications is incorporated by reference herein.

FIELD OF THE INVENTION

The invention relates to pharmacology, medicine, and oncology, and in particular, to prevention and treatment of cancer using mitochondrially-targeted pharmaceutical compositions.

BACKGROUND

Although there are many different anti-tumoral preparations used in clinical practice, their efficiency is in most cases insufficient and the range of diseases sensitive to such therapy is limited. Thus, new, more active preparations, and the development of such compositions which are effective in treating and preventing tumors with primary and gained resistance, remains of current interest.

WO2006005759 reports on mitochondrially-targeted antioxidants application for ontological diseases therapy. This patent states that treatment of mice with tumor xenografts (tumors of epithelial cancers) with mitochondrially-targeted antioxidant MitoQ [current compound is excluded from Applicant's application] leads to tumor size reduction, increased necrosis, and decreased vascularization of the tumor xenografts.

However, no experimental data proving relevance of these statements was shown; examples of pharmaceutical compositions, which could be used for the purpose (including active compound (MitoQ) concentrations), administration methods and doses are not represented in the application as well. Furthermore, no quantitative data on anti-tumoral effect of the used compound were represented. Meanwhile on the current stage of anti-cancer technology, a development quantitative assessment of preparation therapeutic effect is a key factor which determines a possibility of preparation application as an anti-tumoral drug. In addition, the MitoQ composition possesses pro-oxidant influence, which may, indeed, lead to negative consequences, stated by the authors. Thus, WO2006005759 is more about the anti-tumoral effect of mitochondrially-targeted pro-oxidants, and accordingly does not solve the problem of ontological diseases treatment with mitochondrially-targeted antioxidants.

RU 2005132217, filed Oct. 19, 2005, describes the ability of mitochondrially-targeted bioactive compositions to prevent cancer.

SUMMARY

The present disclosure proves a method of treating a cancer in a mammal, comprising administering to the mammal a therapeutically effective amount of a pharmaceutical composition comprising a compound of Structure (I):

wherein A is an effector moiety-antioxidant:

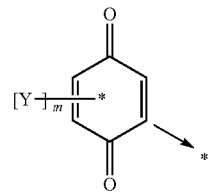

and/or reduced form thereof, wherein m is an integer from 1 to 3; each Y is independently selected from the group consisting of lower alkyl and lower alkoxy; or two adjacent Y groups, together with carbon atoms to which they are attached, form:

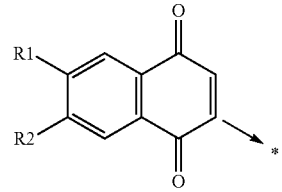

and reduced form thereof, wherein R1 and R2 may be the same or different and are each independently lower alkyl or lower alkoxy; L is a linker group, comprising a straight or branched hydrocarbon chain which can be optionally substituted by one or more substituents and optionally contains one or more double or triple bonds; or a natural isoprene chain; n is integer from 1 to 20; B is a targeting group, comprising $Sk^+Z^-$, wherein $Sk^+$ is a lipophilic cation; and $Z^-$ is a pharmacologically-acceptable anion; with the proviso that in the compound of Structure (I), A is not ubiquinone (e.g. 2-methyl-4,5-dimethoxy-3,6-dioxo-1,4-cyclohexadienyl), tocopherol, or a mimetic of superoxide dismutase or ebselen; when L is a divalent decyl, divalent pentyl, or divalent propyl radical; and when B is a triphenylphosphonium cation, and wherein the compound is not SkQ; and solvates, isomers and prodrugs thereof.

In some embodiments, the cancer treated is lung carcinoma, large intestine carcinoma, cervical carcinoma, skin carcinoma, colon cancer, Lewis carcinoma, fibrosarcoma, osteosarcoma, rhabdomyosarcoma, epithelial carcinoma, neuroblastoma, and lymphoma In certain embodiments, in the compound of Structure (I), A is plastoquinone of the structure:

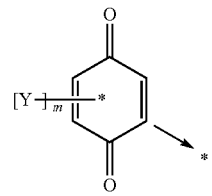

wherein Y is methyl and m=2.

In some embodiments, in the compound of Structure (I), A is methylplastoquinone of the structure:

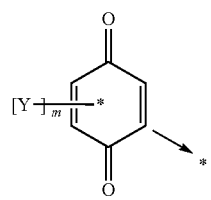

wherein Y is methyl and m=3.

In some embodiments, the compound of Structure (I) is SkQR1, SkQB1, or SkQBP1.

In particular embodiments, the pharmaceutical composition is administered with another anti-cancer therapeutic.

In certain embodiments, the pharmaceutical composition is a solution and is orally administered, parenterally administered, or is transdermally administered and may be ointment, bandage.

In some embodiments, the cancer treated is a Ras-related metastatic cancer.

DESCRIPTION OF THE FIGURES

The patent or application file contains at least one drawing executed in color. Copies of this patent or patent application publication with color drawing(s) will be provided by the Office upon request and payment of the necessary fee.

The foregoing and other objects of the present disclosure, the various features thereof, as well as the invention itself may be more fully understood from the following description, when read together with the accompanying drawings in which.

DESCRIPTION

Figure 1A:
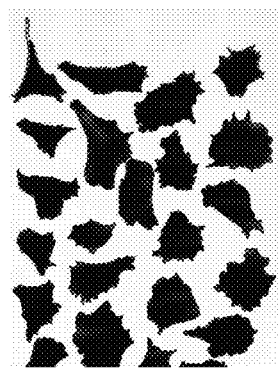
FIGS. 1A-1D are representations of micrographs showing the effect of SkQ1 on the morphology on normal (1B) and Ras-transformed (1D) mouse fibroblasts.
Figure 1C:
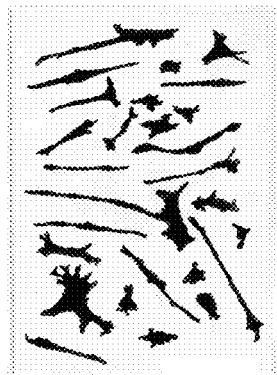
Figure 1B:
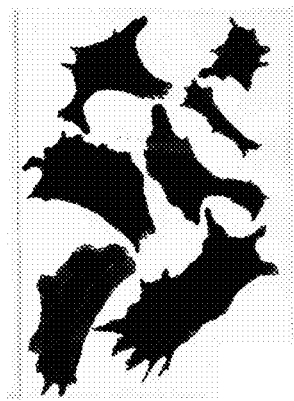
Figure 1D:
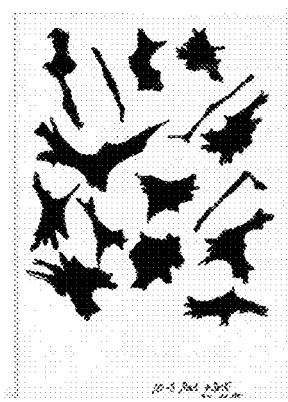

The disclosures of these patents, patent applications, and publications in their entireties are hereby incorporated by reference into this application in order to more fully describe the state of the art as known to those skilled therein as of the date of the invention described and claimed herein. The instant disclosure will govern in the instance that there is any inconsistency between the patents, patent applications, and publications and this disclosure.

Unless defined otherwise, all technical and scientific terms used herein have the same meaning as commonly understood by one of ordinary skill in the art to which this disclosure belongs. The initial definition provided for a group or term herein applies to that group or term throughout the present specification individually or as part of another group, unless otherwise indicated.

The present disclosure relates to the use of pharmaceutical compositions comprising mitochondrially-targeted compounds to treat and prevent oncological diseases.

The composition comprises a targeting moiety, a linker group, and antioxidant. In general, such a compound can be described by the following Structure (I):

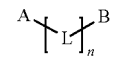

wherein:
A is the effector moiety-antioxidant

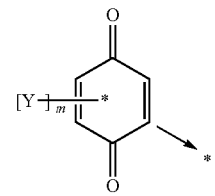

and/or reduced form thereof, wherein:
  m is an integer from 1 to 3;
  each Y is independently selected from the group consisting of: lower alkyl, lower alkoxy; or
  two adjacent Y groups, together with carbon atoms to which they are attached, form a following structure:

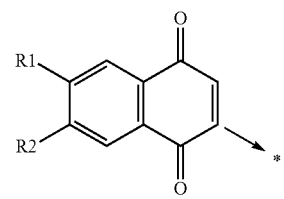

and/or reduced form thereof, wherein:
  R1 and R2 may be the same or different and are each independently lower alkyl or lower alkoxy;

L is a linker group, comprising:
a) a straight or branched hydrocarbon chain which optionally can be substituted by one or more substituents and optionally contains one or more double or triple bonds; or
b) a natural isoprene chain;
n is integer from 1 to 20; and
B is a targeting group comprising $Sk^+Z^-$, wherein:
$Sk^+$ is a Skulachev or lipophilic cation; and
$Z^-$ is a pharmacologically-acceptable anion;
with the proviso that in compound of Structure (I) A is not ubiquinone (e.g. 2-methyl-4,5-dimethoxy-3,6-dioxo-1,4-cyclohexadienyl) or tocopherol or mimetic of superoxide dismutase or ebselen; while L-divalent decyl or divalent pentyl or divalent propyl radical; and while B is triphenylphosphonium cation;
and solvates, isomers and prodrugs thereof.

The pharmaceutical composition can comprise a compound of Structure (I), wherein A is a plastoquinone:

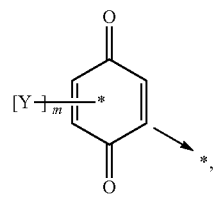

wherein:
Y is methyl and m=2.
Examples of compounds of Structure (I) include, but are not limited to:

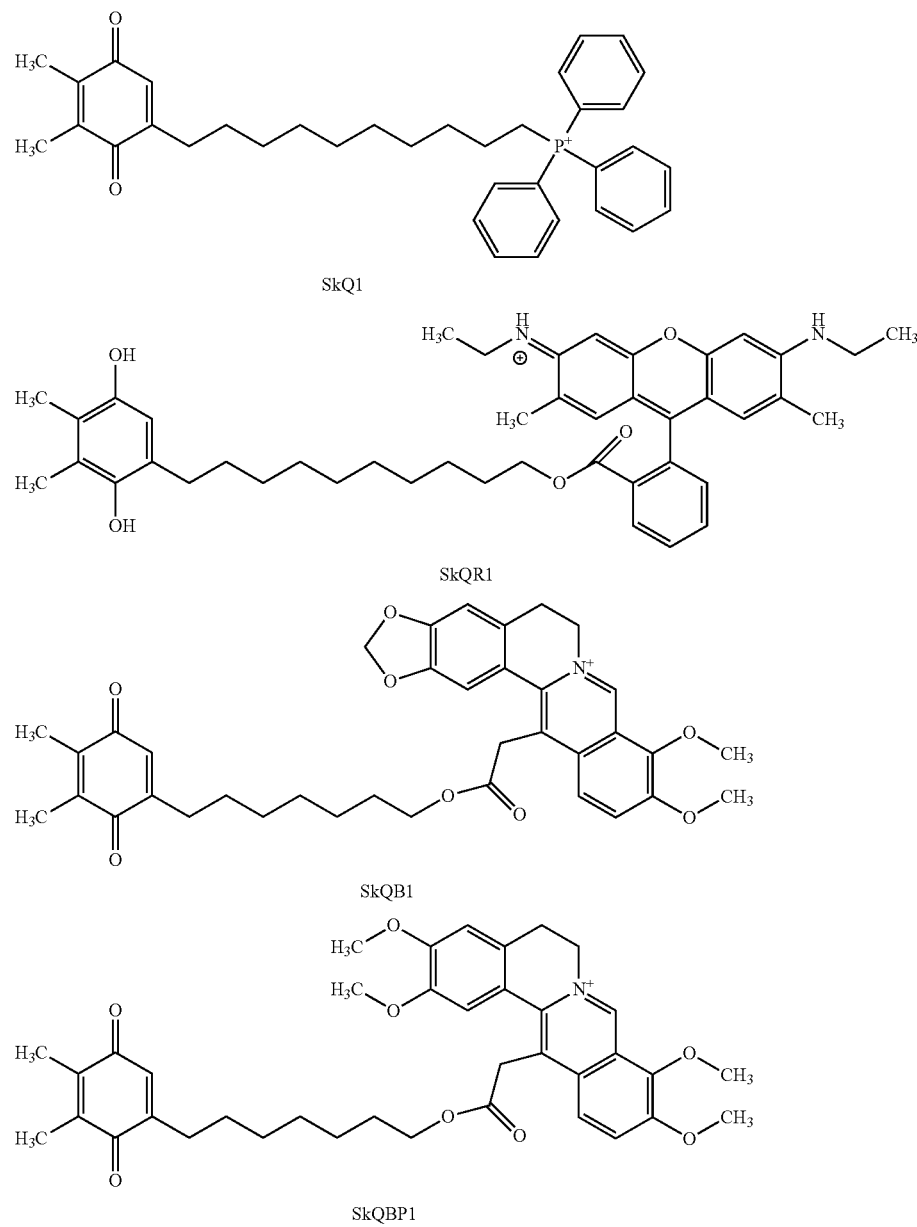

SkQ1

SkQR1

SkQB1

SkQBP1

The pharmaceutical composition for preventing and treatment of oncological diseases also comprises at least one pharmacologically acceptable solvent or carrier. A pharmacologically acceptable solvent or carrier may present filler, a diluent (solvent) or their mixture.

"Therapeutically justified" amount of a compound is an amount of a compound of Structure (I) that causes desired biological or medical response in a patient treated by a doctor or a veterinarian. "Prophylactically justified" amount of a compound is amount of a compound of Structure (I) that prevents or suppresses the disease, or relieves progress of the disease in a patient suffering from a medical state that is tried to be prevented, suppressed or relieved by a doctor or a veterinarian.

Patients to be treated according to the methods of the disclosure include mammals such as humans, monkeys, cows, horses, rabbits, goats, dogs, cats, rats, mice, etc.

The oncological diseases which can be prevented or treated according to the method of the disclosure include, without limitation, malignant growths of lip, mouth cavity, malignant growths of digestive apparatus, malignant growths of respiratory apparatus and thoracic organs, malignant growths of bones and articular cartilages, melanoma and other dermal malignant growth, malignant growths of mesothelial and soft tissues, malignant growth of breast, malignant growth of female reproductive organs, malignant growths of male reproductive organs, malignant growths of urinary tracts, malignant growths of eye, cerebrum and other parts of CNS, malignant growths of thyroid body and other internal secretion glands, malignant growth of roughly specified, postprimary or not specified localizations, malignant growths of lymphoid, hemogenic and their congenial tissues.

Malignant growths of lip, mouth cavity and pharynx include but not limited by lip malignant growths, tongue malignant growths, tongue base malignant growths, malignant growths of non-specified parts of tongue, back of tongue malignant growth, tongue flank malignant growths, tongue lower surface malignant growths, lingual tonsil malignant growths, malignant growth of gingival, mouth floor malignant growths, malignant growths of mouth floor flank, malignant growths of mouth floor forepart, palate malignant growths, kion malignant growths and malignant growths of other non-specified mouth portions, buccal mucosa malignant growths, buccal cavity malignant growths, malignant growths of retromolar area, parotid gland malignant growths, submandibular gland malignant growths, sublingual gland malignant growths, amygdale malignant growths, amygdaloid fossa malignant growths, oropharynx malignant growths, malignant growths of epiglottis fossa, malignant growth of epiglottis forehead, malignant growth of epiglottis flank wall, malignant growths of epiglottis back wall, malignant growths of branchial fissure, rhinopharynx malignant growth, malignant growths of pyriform sinus, malignant growths of pharynx lower part, malignant growth of pharynx lower part back wall.

Malignant growth of digestive apparatus includes but not limited by: malignant growths of esophagus, stomach malignant growths, small intestine malignant growths, dodecadactylon malignant growths, empty intestine malignant growths, twisted intestine malignant growths, malignant growths of Meckel's diverticulum, small intestine malignant growths of non-specified localization, blind intestine malignant growths, vermicular appendix malignant growths, ascending colon malignant growth, malignant growth of segmented intestine hepatic arc, transverse colon malignant growths, malignant growths of segmented intestine lienal arc, descending colon malignant growths, sigmoid colon malignant growths, malignant growths of rectosigmoid junction, straight intestine malignant growths, malignant growths of fundament and anal canal, cloacogenic area malignant growths, malignant growths of liver and intrahepatic biliary tracts, hepatocellular carcinoma, intrahepatic biliary tract cancer, hepatoblastoma, liver angiosarcoma and other liver sarcomas, malignant growths of gall bladder, extrahepatic bile duct malignant growths, malignant growths of major duodenal papilla, pancreatic gland malignant growths, malignant growths of the head of pancreas, malignant growths of the body of pancreas, malignant growths of the tail of pancreas, pancreatic duct malignant growths, pancreatic islet malignant growths, malignant growths of lien.

Malignant growths of respiratory apparatus and thoracic organs includes but not limited by: malignant growths of nasal cavity and middle ear cavity, malignant growths of paranasal sinuses, gorge malignant growths, trachea malignant growths, bronchial and lung malignant growths, thymus malignant growths, heart malignant growths, malignant growths of pleura and inter-pleural space, upper air passages' malignant growths of non-specified localization.

Dermal malignant growths includes but not limited by: malignant melanoma of skin, malignant melanoma of lip, malignant melanoma of eyelid, comprising palpebral commissure, malignant melanoma of ear and external auditory canal, malignant melanoma of head and neck pilous areas, body malignant melanoma, malignant melanoma of upper limb, comprising shoulder joint area, malignant melanoma of lower limb, comprising hip joint and other dermal malignant growths.

Malignant growths of mesothelial and soft tissues include but not limited by: mesothelioma, mesothelioma of pleura, mesothelioma of peritoneum, mesothelioma of pericardium, peripheral nerves, involuntary nervous system and Kaposi's sarcoma, malignant growths of peritoneum and retroperitoneal space, malignant growths of muscle, rhabdomyosarcoma, and other types of malignant growths of connective and soft tissues.

Malignant growths of female reproductive organs include but not limited by: malignant growths of vulva, vaginal malignant growths, malignant growth of uterine cervix, malignant growths of uterine body, ovarian malignant growths, and placenta malignant growths.

Malignant growths of male reproductive organs include but not limited by: malignant growths of phallus, malignant growths of prostate gland, testis malignant growth.

Malignant growths of urinary tracts include but not limited by: malignant growths of kidney, malignant growths of pelvis of kidney, ureter malignant growth, malignant growth of urinary bladder, malignant growth of urethra, malignant growth of Littre's glands.

Malignant growths of eye, cerebrum and other parts of CNS include but not limited by: malignant growths of eye and adventive apparatus, malignant growths of brain tunic, malignant growths of cerebrum, malignant growths of spine, cranial nerves and other segments of CNS, malignant growths of CNS.

Malignant growths of thyroid body and other internal secretion glands include but not limited by: malignant growth of thyroid body, malignant growths of adrenal body, malignant growths of other internal secretion glands and relative formations, malignant growths of parathyroid gland, hypophysis malignant growths, malignant growths of craniopharyngeal duct, malignant growths of epiphysis, malignant growths of intracarotid body, malignant growths of aortic body and other paraganglia.

Malignant growths of lymphoid, hemogenic and their congenial tissues include but not limited by: Hodgkin's disease [megakaryoblastoma], Hodgkin's disease—lymphoid superiority (lymphocyte-rich type), Hodgkin's disease—nodular sclerosis, Hodgkin's disease mixed-cellularity subtype, Hodgkin's disease—lymphocyte-depleted type, other types of Hodgkin's disease, Hodgkin's disease—unspecified type, follicular non-Hodgkin's lymphoma, small cleaved cell lymphoma, follicular, mixed, small cleaved cell lymphoma and large cell, large cell follicular lymphoma, other types of follicular non-Hodgkin's lymphoma, follicular lymphoma non-specified form, diffuse non-Hodgkin's lymphoma, small cell diffuse lymphoma, diffuse small cleaved cell lymphoma, diffuse mixed small and large cell lymphoma, diffuse large cell lymphoma—reticulosarcoma, diffuse immunoblastic lymphoma, diffuse lymphoblastic lymphoma, diffuse non-differentiated lymphoma, Burkitt's lymphoma, diffuse non-specified non-Hodgkin's lymphoma, peripheral and dermal T lymphomas, granulosarcoid, Sézary syndrome, zone T lymphoma, Lennert's lymphoma, peripheral T lymphoma, other non-specified T lymphomas, lymphosarcoma, non-specified T lymphoma, malignant immunoproliferative diseases, Waldenstrom macroglobulinemia, alpha heavy-chain disease, gamma heavy-chain disease, immunoproliferative diseases of small intestine, other immunoproliferative diseases, multiple myeloma and malignant cell plasma growths, plasma cell leukemia, plasmacytoma, extramedullary plasmacytoma, lymphocytic leukemia, acute lymphoblastic leukemia, inveterate lymphoblastic leukemia, prolymphocytic leukemia, hairy-cell leukemia (leukemic reticuloendotheliosis), adult T cell leukemia, myeloblastosis, acute myeloblastosis, inveterate myeloblastosis, subacute myeloblastosis, myeloid sarcoma (green cancer—chloroma, granulocytic sarcoma), acute progranulocytic leukemia, acute myelomonocytic leukemia, monocytic leukemia, acute monocytic leukemia, inveterate monocytic leukemia, subacute monocytic leukemia, acute erythremia and erythrolcukemia, inveterate erythremia, acute megakaryoblastic leukemia, mast cell leukemia, acute panmyeloleukemia, acute myelofibrosis, Letterer-Seve disease (non-lipidic reticuloendotheliosis, reticulosis), malignant histiocytosis, malignant mast cell tumor, pure histiocytic lymphoma.

Compositions of Structure (I) can be used for efficient preventing and therapy of all types of cancer alone or in combination with other forms of cancer therapy such as chemotherapy and/or irradiation, and/or antibody therapy.

Application of pharmaceutical compositions related to the invention can be both systemic and local. Methods of administration comprise enteral, such as oral, sublingual and rectal; local, such as percutaneous, intradermal and oculodermal, and parenteral. Acceptable parenteral administration methods comprise injections, such as endovenous, intramusculary, hypodermic, intraperitoneal, intra-arterial etc injections, and non-injectional methods, such as intravaginal and nasal. Preferably compounds and pharmaceutical compositions, related to present invention, should be administrated parenteral and per oral. In particular, order can be done in form of intravenous injections or tablets, granules, capsules or any in different pressed compressed form.

When a compound of Structure (I) is administered as a pharmaceutical composition, the compound should be mixed according to formula with a suitable amount of pharmacologically acceptable solvent or carrier so that to have the appropriate form for administration to a patient. The term "solvent" relates to diluent, auxiliary medicinal substance, filler or carrier which is mixed with the compound of Structure (I) for administration to a patient. Liquids like water, and oils including petrolic, animal, vegetative and synthetic such as peanut oil, soybean oil, mineral oil and other similar oils can be used as said pharmacological carriers. Normal saline solution, acacia pitch, gelatin, starch, talc, keratin, colloid silver, urea etc can serve as said pharmacological solvents. Said composition can also include auxiliary substances, stabilizers, thickeners, lubricant and coloring agents.

The compounds and compositions of the present invention can be administered in the form of capsules, tablets, pills, pellets, granules, syrups, elixirs, solutions, suspensions, unctures, creams, sprays, emulsions, suppositories, retarded release substances, or in any other form suitable for administration to a patient. A further aspect of present invention is application of compounds of Structure (I) and pharmaceutical compositions in form of solutions for per oral or parenteral administration.

A therapeutically effective amount of a compound of Structure (I) for treatment of a specific cancer depends on the type and nature of the cancer, its size, progress, and metastatic state, and should be determined at consultation with a physician in charge. Representative, nonlimiting acceptable doses for per oral administration are from about 0.025 µg/kg to about 120 mg/kg patient weight, from about 25 µg/kg to about 50 µg/kg patient weight, or about 25 µg/kg patient weight or about 50 µg/kg patient weight. Representative, nonlimiting acceptable doses for endovenous administrations are from about 0.1 µg/kg to about 10 mg/kg patient weight, from about 25 µg/kg to about 125 µg/kg patient weight, or about 25 µg/kg patient weight or about 125 µg/kg patient weight.

The following are examples of acceptable pharmaceutical compositions for oral administration:

Pharmaceutical Composition-1—Gelatinous Capsules

| Ingredient | Amount (mg/capsule) |
| --- | --- |
| Composition of Structure I | 0.0015-1000 |
| Amylum | 0-650 |
| Amylum powder | 0-650 |
| Liquid silicone | 0-15 |

Pharmaceutical Composition-2—Tablets

| Ingredient | Amount (mg/capsule) |
| --- | --- |
| Composition of Structure I | 0.0015-1000 |
| Microcrystalline cellulose | 200-650 |
| Silicon dioxide powder | 10-650 |
| Stearic acid | 5-15 |

Pharmaceutical Composition-3—Tablets

| Ingredient | Amount (mg/capsule) |
| --- | --- |
| Composition of Structure I | 0.0015-1000 |
| Amylum | 45 |
| Microcrystalline cellulose | 35 |
| polyvinylpyrrolidone (10% aqueous solution) | 4 |
| Carbossimetilcellulose sodium salt | 4.5 |
| Talc | 1 |
| Magnesium stearate | 0.5 |

Pharmaceutical Compulsion-4—Suspensions

| Ingredient | Amount (mg/5 ml) |
| --- | --- |
| Composition of Structure I | 0.0015-1000 |
| Sirup | 1.25 |
| Benzoic acid solution | 0.10 |
| Carbossimetilcellulose sodium salt | 50 |
| Flavor additive | if necessary |
| Food grade dye | if necessary |
| Water (distilled) | Up to 5 ml |

The following are examples of acceptable pharmaceutical composition for administration in form of an aerosol or spray:

| Ingredient | Amount (percent by weight) |
| --- | --- |
| Composition of Structure I | 0.0025 |
| Etanol | 25.75 |
| Difluorochloromethane | 70 |

The following is an example of acceptable pharmaceutical composition for administration in form of suppositories:

| Ingredient | Amount (mg/suppository) |
| --- | --- |
| Composition of Structure I | 1 |
| Saturated fatty acid glyceride | 2000 |

The following is an example of acceptable pharmaceutical composition for administration in form of solution for application per os (pH 6.5):

| Ingredient | Amount |
| --- | --- |
| Composition of Structure I | 5 mg |
| Isotonic solution | 1000 ml |

Reference will now be made to specific examples illustrating the disclosure. It is to be understood that the examples are provided to illustrate exemplary embodiments and that no limitation to the scope of the disclosure is intended thereby.

EXAMPLES

Example 1

Effect of SkQ1 on Ras-Transformed Epithelial Cells Morphology and Adherence

The experiment was carried out using cells, transformed with genetic construct, expressing oncogene RAS, and thus modeling conditions of cells underwent cancerous transformation. (see, model description in Levina, et al. (1996), *Exp. Cell. Res.*, November 25; 229(1):159-165).

Figure 2:
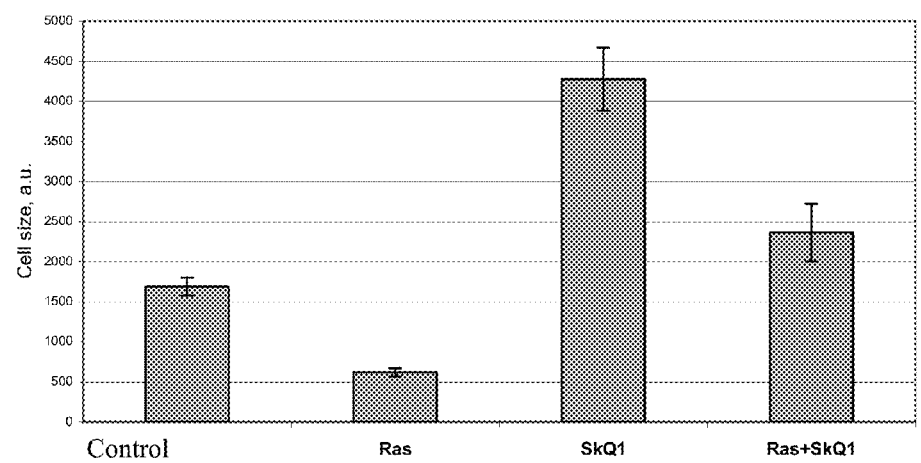
FIG. 2 is a graphic representation showing the effect of SkQ1 on surface area of normal and Ras-transformed mouse fibroblasts

Mouse Ras-transformed fibroblast cells had strongly expressed changed morphology (FIG. 1), one close to morphology of metastasizing cancerous cells (decrease in surface square, cell elongation). Morphological analysis demonstrated cell surface square mean values to be significantly decreased in comparison to control (FIG. 2.). Cytoskeleton elements and focal contact proteins—vinculin and paxillin—content was drastically decreased in these cells. Cells were poorly adherent and spread-eagled what led to monolayer structure disorder. All these features are peculiar for metastasizing cancerous cells with comparatively increased mobility.

However incubation with SkQ1 led to significant changes in cells morphology (FIG. 1). Mean cell surface square value increased manifold (FIG. 2). Morphological changes correlated with actinic fibrils increase in content, focal contact reinforcement and cell better adherence to the surface. Ras-transformed fibroblasts treated with SkQ1 formed monolayers similar to those of normal fibroblasts.

These obtained results demonstrate that in the model system, treatment of metastasizing cancerous cells with SkQ1 led to normalization of this condition.

Example 2

Study of SkQ1 Anti-Tumoral Activity on A-431 Human Skin Cancer Heteroxenografts Transplanted to HIV Mice This experiment was carried out taking into account the Russian Federation Ministry of Health Care and international recommendations, published Treshchalina, et al., "Methodical Recommendations on the Study of Anti-Tumoral Activity of Pharmacological Substances," *Guidance on Experimental (Preclinical) Study of New Pharmacological Substances* (ed. Habriev RU) (2005); "USSR and Clinical Correlations," *NCI Monograph* 55 (1980); *Survey and Antitumor Toxicity Test Systems*, EORTC Screening and Pharmacology Group (1989); *Anticancer Drug Development Guide Preclinical Screening, Clinical Trials, and Approval*, (ed. Teicher) (1997).

Treatment Preparation

Before administration, SkQ1 was diluted with sterile physiological saline up to 0.5 μM and 5.0 μM. The preparation was injected intraperitoneally as single doses of 5.0 nM/kg and 50.0 nM/kg, 0.2 ml/mouse.

Tumor Cell Culture

The experiment was carried out using the A-431 cell line [1], lodged in the Russian collection of cell cultures, and which possessed the following features:

Origin: human, epithelial carcinoma J. Natl. Cancer Inst. (1973) 51:1417-1423.

Morphology: epithelial.

Cultivation method: monolayer.

Cultivation conditions: 10% bovine embryonal serum DMEM culture.

Procedure of seeding: cell removal using 0.25% trypsin, 0.02% versene (3:7), ratio of seeding 1:3 1:6, optimal density $2.04.0 \times 10^4$ cell per $sm^2$ cryopreservation media, 10% DMSO, $1.0 \times 10^6$ cells/ml per ampoule.

Viability after cryopreservation: 83% (trypan blue staining on zero passage)

Contamination control: no bacteria, fungi or micoplasma detected

Genetic identity control: karyological, enzymatic (LDH, G6PDH) analysis.

Karyology: 2n-46, chromosome variability limit 5777, chromosome modal number 6871

Tumorigenicity: tumorigenic in HIV mice and in mice treated with antithymocyte serum.

Other features: large number of receptors to epidermal growth factor.

Application area: growth factors study, cell biology.

Collection: ATCC CRL 1555; ECACC 85090402; INC RAS.

A-431 cells were grown on RPMI-1640 medium that contained 10% calf serum and 1 mM glutamine. Cells were transferred to a flask at a ratio of 1:2 or 1:3 from full monolayer. The medium was changed every 2 to 3 days. A cultivated cell suspension was then used to engraft HIV mice.

Mammals and Implanted Tumors

The experiment was performed using HIV female mice Balb/c nude at the age 8 to 9.5 weeks. All mice were raised in GU RONC. Mice were managed in specialized virus-free chamber with sterile aeration, fed with sterile briquette food and water under normalized temperature condition and moisture.

Cells of A-431 cell line were hypodermically implanted only once in number $1.7-1 \times 10^6$ per mouse in 0.2 ml of RPMI-1640 nutrition medium.

Anti-Tumoral Effect Estimation

Anti-tumoral effect estimation was carried out using common rate T/C (Treatment/Control), evaluated as a ratio of average tumor volumes in treated and control groups given in percents. Rate was taken evaluated using the following formula T/C %=(Vo/Vk)/(Vk)×100%, where Vo and Vk are the mean volumes of tumor in treated and control groups thereof. Thus, in the control group, T/C=100%. Mean volume was evaluated using the following formula: Vm (mm³)=axbxc. T/C≤42% was taken as a minimal efficiency criterion (*Anticancer Drug Development Guide* (1997) (ed. B. A. Teicher) Humana Press, Totowa, N.J., pp. 101-125). To analyze the speed of growth (standarcy value), a ratio of mean tumor relative to the first one taken was determined as follows.

Evaluation started after the appearance of a palpable tumor (9 days after implantation). After that multiple tumor volume evaluations were performed until the 20th day after transplantation. The first evaluation of treated groups was performed during treatment, and the next three evaluations were performed during 6 days after end of the treatment. Tumor evaluations were stopped on the 21st to the 24th day after the first mouse died in three experiments.

Tolerance to the treatment was estimated according to the time of death which corresponded to the treatment with each preparation.

Histological Research

Mice were sacrificed by ether anesthesia overdose. An autopsy was performed, and tumors were then extracted and assayed histologically and immunohistochemically. Tumors were fixed in 10% formaldehyde and set into paraffin wax. Histological assays were carried out on tumor histological sections, stained with hematoxylin and eosin. The number of microvessels was examined by standard immunological method using antibodies to CD34 antigen. Presence of vessel mimicry was estimated by tumor section staining with Schiffs reagent.

Study of anti-tumoral activity was performed in three experiments.

Experiment 1

At day "zero," all the mice were hypodermically engrafted with cells of the A-431 cell line at a concentration of $1.7 \times 10^6$ per mouse in 0.2 ml of RMP1-1640 nutrition medium. After implantation all mice were divided into groups of 7 mice.

Two of the study groups intraperitoneally received the SkQ1 preparation every day from day 1 to day 14 after tumor implantation: Group 1 (control) mice (average weight 20.3 [19.6÷21.0]g), intraperitoneally received 0.2 ml of physiological saline from the 1st to the 14th day after tumor implantation; Group 2 mice (average weight 19.9 [19.2÷20.6] g), intraperitoneally received SkQ1 preparation in a single dose of 5.0 nM/kg (sum dose 70.0 nM/kg) from the 1st to the 14th day after tumor implantation; Group 3 mice (average weight 19.8 [19.1÷20.5]g), intraperitoneally received SkQ1 preparation in a single dose of 50.0 nM/kg (total dose 700.0 nM/kg) from the 1st to the 14th day after tumor implantation.

In Group 1 (control), the mean tumor volume values (Vm) comprised 458 [318÷598] mm³, 1295 [959÷1631] mm³, 1996 [1319÷2673] mm³, and 2564 [2064÷3064] mm³ on the 9th, 14th, 17th, and 20th day after transplantation. The ratio of mean volumes of growing tumors comprised, correspondingly, 2.83-4.36-5.6 times. Growths factors demonstrate tumor development speed to be normal for mice hypodermic tumors in the 20-day period.

The first mouse died on the 22nd day after tumor transplantation. An autopsy revealed no visual signs of pathological changes in its organs. The remaining mice were sacrificed on the 23rd day after transplantation. Again, autopsy demonstrated no pathological changes in their organs.

In Group 2 (SkQ1 preparation in single dose 5.0 nM/kg), the mean tumor volume values (Vm) comprised 289 [87÷1491] mm³, 955 [515÷1395] mm³, 1349 [903÷1793] mm³ and 1863 [919÷2807] mm³ on the 9th, 14th, 17th, and 20th day after transplantation. The anti-tumoral effect at these stages comprised T/C=63%, 74%, 67%, and 73% thereof. No statistical differences compared with the control group were found (p>0.05). Treatment tolerance was satisfactory. Mice started to die on the 7th and 8th day after the end of the treatment. Two mice died on the 21st and 22nd day after transplantation. An autopsy revealed no visual signs of pathological changes in their organs. The remaining mice were sacrificed on the 23rd day after transplantation. Again, autopsy demonstrated no pathological changes to their organs.

In Group 3 (SkQ1 preparation in single dose 50.0 nM/kg) the mean tumor volume values (Vm) comprised 730 [430÷1030] mm³, 2078 [1328÷2828] mm³, 2678 [1667÷3689] mm³ and 3557 [2042÷5072] mm³ on the 9th, 14th, 17th, and 20th day after transplantation thereof. The anti-tumoral effect at these stages comprised T/C=159%, 160%, 134%, and 146% thereof. Treatment tolerance was satisfactory. All mice were sacrificed on the 23rd day after transplantation. An autopsy demonstrated no pathological changes in their organs.

In summary, in Group 3, mice which received treatment of the SkQ1 preparation in a single dose 50.0 nM/kg, T/C comprised 134%-160%, which is evidence of potential stimulation of tumor growth.

In Group 2, after 8 injections of the SkQ1 preparation in single dose of 5.0 nM/kg, tumor growth was inhibited and T/C comprised 63%. Total dose up to the moment of the effect seen comprised 40.0 nM/kg. Further injections led to no additional effect, and no growth acceleration was seen. Thus, the preparation can be effective when given 8 times as single dose of 5.0 nM/kg (total dose 40.0 nM/kg).

Experiment 2

On day "zero," all mice were hypodermically engrafted with cells of the A-431 cell line at a concentration of $1.0 \times 10^6$ per mouse in 0.2 ml of RPMI nutrition medium. After implantation all mice were divided in 2 groups of 10 mice.

Group 1 (control) mice (average weight 20.8 [19.8÷21.8] g), intraperitoneally received 0.2 ml of physiological saline from the 1st to the 8th day after tumor implantation.

Group 2 mice (average weight 20.1 [19.6÷20.6]g), intraperitoneally injected with the SkQ1 preparation in a single dose of 5.0 nM/kg (sum dose 40.0 nM/kg) from the 1st to the 8th day after tumor implantation.

In the Group 1 (control) mice, mean tumor volume values (Vm) comprised 155 [117÷193] mm³, 1008 [828÷1188] mm³, 1641 [1152÷2130] mm³, and 2936 [2261÷3611] mm³ on the 8th, 14th, 17th, and 24th day after transplantation thereof. The ratio of the mean volumes of the growing tumors comprised correspondingly 6.5-10.5-18.9 times. Growth factors demonstrate a comparatively high speed of tumor development in this experiment.

The first mouse died on the 24th day after tumor transplantation. An autopsy revealed no visual signs of pathological changes to its organs. The remaining mice were sacrificed on the 24th day after transplantation. Again, an autopsy demonstrated no pathological changes to their organs.

In the Group 2 (SkQ1 preparation in single dose 5.0 nM/kg) mice, mean tumor volume values (Vm) comprised 95 [55÷135] mm³, 724 [441÷1007] mm³, 1582 [1007÷2157] mm³, and 2953 [1730÷4176] mm³ on the 8th, 14th, 17th, and 24th day after transplantation thereof. The anti-tumoral effect at these stages comprised T/C=61%, 72%, 96%, and 101% thereof. One mouse died on the 16th day after treatment end and on the same day as one mouse died in the control group. An autopsy of dead and sacrificed mice revealed no visual signs of pathological changes to their organs.

The results demonstrate that an 8-day treatment with 5.0 nM/kg single dose of the SkQ1 preparation to HIV mice with human skin cancer A-431 heteroxenografts led to replicable inhibition of tumor growth (T/C=61%).

Experiment 3

On day "zero," all mice were hypodermically engrafted with cells of the A-431 cell line in concentration 1.0×10⁶ per mouse in 0.2 ml of RPMI nutrition medium. After implantation, all mice were divided into 2 groups of 9 mice.

Group 1 (control) mice (average weight 18.8 [18.3÷19.3] g), intraperitoneally received 0.2 ml of physiological saline from the 1st to the 8th day after tumor implantation. Group 2 mice (average weight 18.8 [18.3÷19.3]g), were intraperitoneally injected with SkQ1 preparation in single dose 5.0 nM/kg (sum dose 70.0 nM/kg) from the 1st to the 14th day after tumor implantation.

In Group 1 (control) mice, the mean tumor volume values (Vm) comprised 94 [9÷179] mm³ and 567 [27÷1107] mm³ on the 14th and 21st day after transplantation thereof. Growth factors demonstrate a comparatively low speed of tumor development in this experiment. The first mouse died on the 21st day after tumor transplantation. An autopsy revealed no visual signs of pathological changes in its organs. The remaining mice were sacrificed on the 23rd day after transplantation. Again, autopsy demonstrated no pathological changes to their organs.

In Group 2 (SkQ1 preparation in single dose 5.0 nM/kg) mice, the mean tumor volume values (Vm) comprised 39 [6÷72] mm³ and 256 [94÷418] mm³ on the 14th day and 21st day after transplantation thereof. Immediately after the end of the treatment a significant anti-tumoral effect was seen. T/C comprised T/C=41%.

Tolerance to the treatment was satisfactory. The first mouse died on the 7th day after the end of treatment. An autopsy of dead and sacrificed mice revealed no visual signs of pathological changes in their organs.

The results demonstrate that immediately after the end of the 14-day treatment with 5.0 nM/kg single dose of SkQ1 preparation, HIV mice with human skin cancer A-431 heteroxenografts possessed minimal anti-tumoral effect. T/C=42%.

Histological and immunohistochemical analyses of tumor sections were performed on material obtained in experiment 1.

Histological assay revealed that tumor xenografts possess typical structure of non-differentiated tumor of epithermal type. Comparison of control samples with those of Group 2 demonstrated that SkQ1 preparation in a single dose of 5.0 nM/kg causes partial tumor differentiation: signs of keratinization appear in tumor tissue.

The number of microvessels was counted in so-called "hot spots" (tumor areas with maximal vascularization). The number of microvessels in tumors on the 23rd day and the 9th day after end of the treatment did not statistically differ in the three groups. However, microvessels in Group 2 were found to be of smaller diameter than in the control group.

Sample staining with PAS reagent revealed tumors in control group to possess signs of vasculogenic mimicry, while no such signs were seen in tumors in Group 2.

This study of the effect of SkQ1 treatment on HIV mice with human skin cancer A-431 hypodermic xenografts revealed that long-termed injection of SkQ1 in single doses of 5.0 nM/kg did not cause tumor growth acceleration, and in some cases led to 50% inhibition of growth. Injection of SkQ1 in single doses of 5.0 nM/kg causes partial differentiation of A-431 tumor tissue, decreasing signs of vasculogenic mimicry, though did not affect the total number of microvessels.

Example 3

Study on SkQ1 Preparation Anti-Tumoral Effect on Mice Tumors (Hypodermic Introduction of Ehrlich's Carcinoma The experiment was performed according to the methods described in Example 2.

Injection of the preparation started 48 hours after transplantation and proceeded during 5, 10, 15, and 30 days. For tumor treatment efficiency, estimations of tumor volumes were evaluated many times after end of short courses or once after end of the 30-day course. Efficiency was judged according to standard tumor growth suppression factor (TGS) in comparison to control group that did not receive a treatment and results were calculated in percents. The results were then statistically calculated using confidence intervals of mean values of compared values, difference stated reliable if $p<0.05$. The results are shown in Table 1.

TABLE 1

| | | | Way of | Day after transplantation | | |
|---|---|---|---|---|---|---|
| Number of mice | Single dose | Day of therapy | introduction | 7 | 14 | 21 |
| | | Control, ph. s. 15 days | | | | |
| N = 10 | Ph. s. 0.2 ml | — | ip | 416 [328 ÷ 504] | 716 [543 ÷ 889] | 1188 [460 ÷ 1916] |

TABLE 1-continued

| Number of mice | Single dose | Day of therapy | Way of introduction | Day after transplantation | | |
|---|---|---|---|---|---|---|
| | | | | 7 | 14 | 21 |
| SkQ1 preparation, 5-day course | | | | | | |
| N = 10 | 0.5 nM/kg | 2-7 | ip | 251 [134 ÷ 368] | 547 [319 ÷ 775] | 1000 [462 ÷ 1538] |
| TGS%* | | | | 40 | 23 | 16 |
| SkQ1 preparation, 10-day course | | | | | | |
| N = 10 | 0.5 nM/kg | 2-13 | ip | 228 [120 ÷ 336] | 474 [210 ÷ 738] | 853 [299 ÷ 1407] |
| TGS% | | | | 45 | 34 | 28 |
| SkQ1 preparation, 15-day course | | | | | | |
| N = 10 | 0.5 nM/kg | 2-16 | ip | 259 [150 ÷ 368] | 459 [319 ÷ 599] | 838 [945 ÷ 1131] |
| TGS% | | | | 38 | 36 | 29 |

As was demonstrated, SkQ1 preparation in a single dose of 0.5 nM/kg possessed short-time inhibition effect on tumors of mice with hypodermic Ehrlich's carcinoma immediately after the end of the 5-day course (TGS=40%-50%). A ten-fold dose increase or increase of injection number did not lead to prolongation of said effect. Thus, the 5-day treatment course should be considered as minimal efficient course.

Example 4

Study of the Anti-Tumoral Effect of SkQ1 on Human Large Intestine Carcinoma

Two human large intestine carcinoma cell sub-lines that differ by p53 status—wild type cells (HCT116 p53+/+)) and cells with inactivated p53 (HCT116 p53−/−)) cell line cultivation see in Bunz et al. (1998) Science, 282:1497-1500; see model description in Sablina et al. (2003), *J. Biol. Chem.*, 278:27362-27371. One million cells were hypodermically implanted into thymus-deprived mice. Mice in each group were divided into 4 sub-groups of 10 mice: one group received water to drink; one group received water with SkQ1 (0.01 nmol) per mouse per day (0.5 nM/kg/day); one group received water with SkQ1 (0.1 nmol) per mouse per day (5 nM/kg/day); one group received water with SkQ1 (1 nmol) per mouse per day (50 nM/kg/day).

The size of the tumors was evaluated every 3 days. After 4 weeks mice were sacrificed and the tumors removed and fixed for histological assay.

Figure 3A:
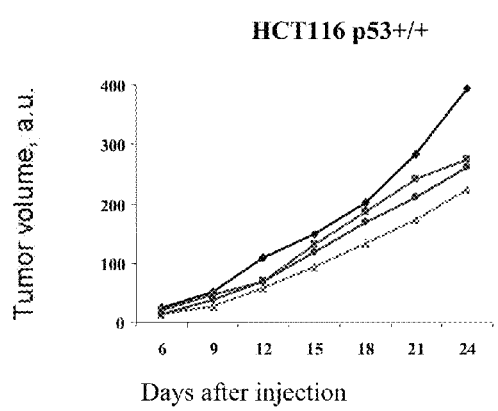
FIGS. 3A and 3B are graphic representations showing the effect of SkQ1 on the growth of tumors from HCT116-p53 wt and HCT116-p53−/− cell lines
Figure 3B:
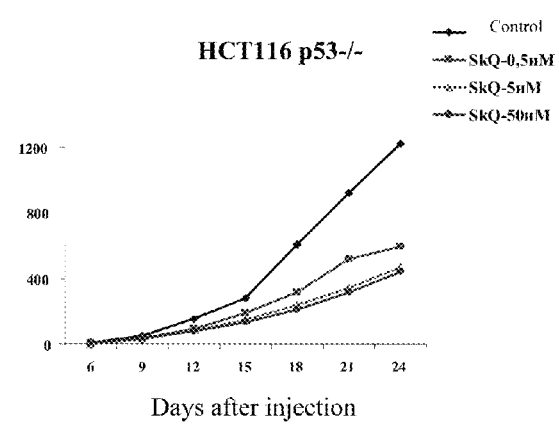
Figure 4A:
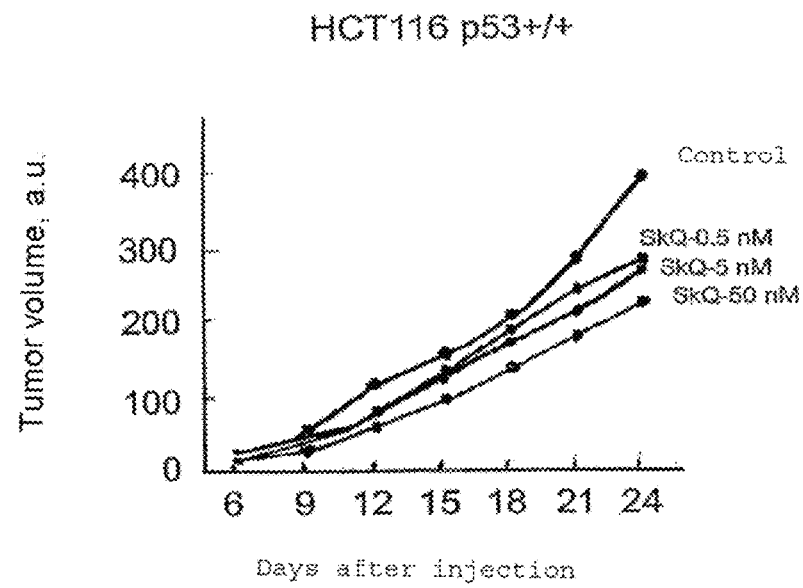
FIGS. 4A and 4B are graphic representations showing the effect of SkQ1 on growth of HCT116 xenografts.
Figure 4B:
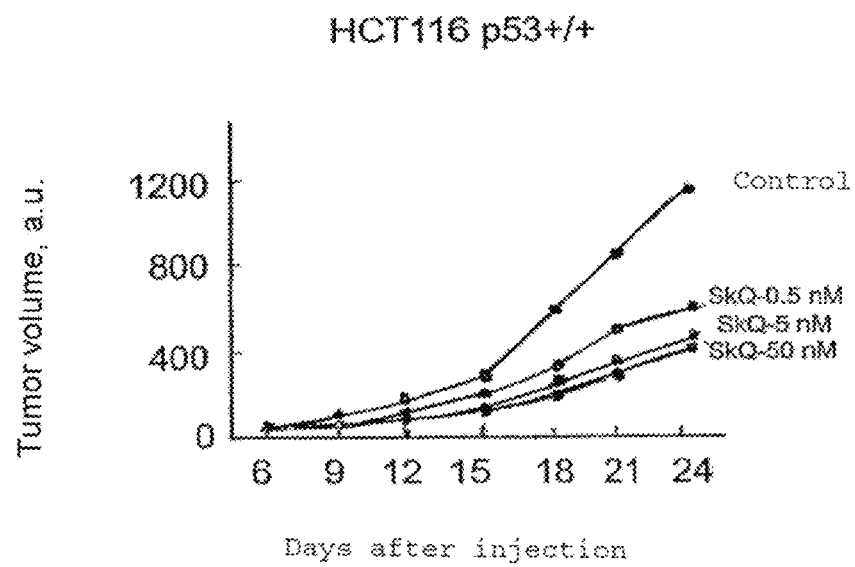

According to the data obtained, the addition of the SkQ1 preparation to drinking water led to suppression of tumor growth in comparison to the control group that received pure water. Changes in speed of growth were significantly higher in tumors with inactivated p53 than in tumors with wild type (WT) p53 (FIG. 3). An efficient concentration appears to be 0.1 nmol per mouse per day (5 nM/kg/day). The data demonstrates that SkQ1 has a stronger effect on the tumor with inactivated p53 compared to tumors with WT p53.

Example 5

Development of Joined Therapy with SkQ1 and Doxorubicin Chemotherapy

For development of oncological diseases joint therapy that combines SkQ1 and chemotherapy, a study on SkQ1 influence on single doxorubicin injection efficiency was performed (one of the mechanisms of the preparation is activation of oxidative processes in normal and cancerous cells). SkQ1 was introduced before, simultaneously, or after introduction of doxorubicin in maximum dose of 500 nM/kg (in order to block oxidative mechanism of doxorubicin influence).

Table 2 shows the effect of joint introduction of 500 nM/kg SkQ1 in 0.2 ml per mouse for days in the form of an alcohol solution and doxorubicin introduced in all variants intraperitoneally in a dose of 7 mg/kg on the 7th day after transplantation. Doxorubicin was applied before, after, and during the course of SkQ1.

TABLE 2

Effect of SkQ1 (Alcohol Solution) Combined With Doxorubicin on Growth of Lung Lewis's Carcinoma

| Group | Dose mg/kg, regime and way of introduction | TGS %, by tumor volume Days | | | | |
|---|---|---|---|---|---|---|
| | | 7 | 10 | 14 | 17 | 21 |
| Control[1] | 0.2 ml/mouse alcohol solution per.os. × 10 | 199 ± 66 | 1006 ± 182 | 3034 ± 354 | 5596 ± 1100 | 10575 ± 3243 |
| SkQ | 500 nmol, 0.2 ml/mouse per.os. × 5 (2-6 days) | 33 | 42 | 48 | 28 | 30 |
| DOX | DOX(7 mg/kg × 17th day ip | —[2] | 26 | 38 | 35 | 30 |

TABLE 2-continued

Effect of SkQ1 (Alcohol Solution) Combined With Doxorubicin on Growth of Lung Lewis's Carcinoma

| Group | Dose mg/kg, regime and way of introduction | TGS %, by tumor volume Days | | | | |
|---|---|---|---|---|---|---|
| | | 7 | 10 | 14 | 17 | 21 |
| SkQ + DOX | 500 nmol, 0.2 ml/mouse per.os. x 5 (2-6 days) + DOX (7 mg/kg x 17$^{th}$ day ip | 39[2] | 61 | 58 | 51 | 50 |
| SkQ + DOX + SkQ | 500 nmol, 0.2 ml/mouse per.os. x 5 (5, 6, 7, 8, 9) + DOX (7 mg/kg x 17$^{th}$ day ip | —[2] | 23 | 37 | 23 | 29 |
| DOX + SkQ1 | DOX (7 mg/kg x 17$^{th}$ day ip 500 nmol, 0.2 ml/mouse per.os. x 5 (8, 9, 10, 11, 12) | —[2] | 18 | 24 | 28 | 6 |

[1]As a control - volumes of tumors in control group are given in mm3
[2]day of doxorubicin introduction As shown above, SkQ1 monotherapy suppressed 33% of tumor growth when measured immediately after the end of the course. The anti-tumoral effect of doxorubicin, applied on the 7th day when the tumor was already fully developed was less expressed. TGS comprised 26% and 36% on the 10th and 14th day thereof.

The most efficient joint treatment appears to be a SkQ1 and doxorubicin scheme with a 5-day-long course of SkQ1 before the introduction of doxorubicin. Maximal TGS was seen on the 10th day (61%) and stayed up to the 21st day. The effect of SkQ1 on the 7th day was the same in Groups receiving SkQ1 as monotherapy, and in Groups receiving doxorubicin after that: TGS comprises 33% and 39% thereof.

Thus, an efficient scheme introduces doxorubicin after a 5-day-long course of SkQ1. Addition of SkQ1 to drinking water appeared to increased HIV mice immunity to infectious diseases, as determined by estimation of mouse life-span when managed in a chamber without sterile aeration.

SkQ1 efficiency was demonstrated to depend on p53 status in the tumor. Addition of the SkQ1 preparation (maximal effect—5 nM of SkQ1) to drinking water inhibited the growth of tumors with inactivated p53 than in tumors having WT p53.

The application of SkQ1 (500 nM, 5-day-long course) before the introduction of doxorubicin appears to be effective (maximal TGS was seen on the 10th day (61%) and remains the same until the 21st day). Different schemes of combination therapy where the application of doxorubicin is done before or during the SkQ1 course appear to be ineffective.

Example 6

Treatment of Rhabdomyosarcoma with SkQs

Rhabdomyosarcoma is a cancer which develops in skeletal muscle. Its etiology is unknown. Although it can occur in many places in the body, it is most often found in the muscles of the neck and head, urogenital tract, and the arms or legs. The cancer develops in rhabdomyoblasts which are the embryonic cells that will eventually form skeletal muscles. Although rhabdomyo-sarcoma is found in adults, it more commonly develops in infants and young children, and is the most common soft tissue tumor in children.

There are three types of rhabdomyosarcoma: embryonal (ERMS), alveolar (ARMS), and anaplastic rhabdosarcoma. ERMS is the most common type of rhabdomyosasrcoma and is usually found in infants and young children. ERMS cells look like muscle cells of a 6- to 8-week-old fetus. There are 2 subtypes of ERMS (botryoid and spindle cell) which tend to have a better prognosis than other types of ERMS. ARMS affects older children and teens and more often occurs in the large muscles of the trunk, arms, and legs. ARMS cells look like the muscle cells of a 10-week-old fetus. As it grows faster than ARMS, it often requires more intensive treatment. Anaplastic rhabdomyosarcoma is an uncommon cancer that occurs in adults, but rarely in children. It is a fast-growing cancer that often occurs in hard-to-treat parts of the body.

Aggressive treatment of rhabdomyosarcoma is required and includes irradiation, chemotherapy (with dacarbazine, doxorubicin, epirubicin, gemiatabine, or ifosfamide), or both before and after surgical removal of the tumor. Side-effects of these treatments are common. The prognosis depends on the specific type of tumor, its size and location, and its level of metastasis. In addition, children 1 to 9 years of age have better survival rates that infants, older children, and adults.

In the following experiment, a human rhabdomyosarcoma cell line (RD) purchased from the ATCC (#CCL-136) was used. These cells were isolated from a Caucasian female 7 years ago and are widely accepted as a model for studies of rhabdomyosarcoma in vitro and in vivo.

The cells were grown in Dulbecco's modified Eagle's medium (DMEM, Gibco®, Invitrogen, Carlsbad, Calif.) supplemented with 10% FBS. The cells were treated with 20 nM SkQ (SkQ1, SkQR1, SkQB1, or SkQBP1), or with a non-targeted antioxidant (1 mM NAC, or 100 μM Trolox) 24 to 72 hours before evaluation. In some experiments 1 μM of the protonophorous uncoupler FCCP was added 1 hour before the addition of SkQ1 to depolarize the mitochondrial membrane, and thus to prevent the electrophoretic accumulation of SkQ in the mitochondrial interior. The cells were then stained with rabbit polyclonal antibodies against actin (1:1000) (Sigma-Aldrich Corp., Baleras, Russia) and monoclonal antibody DM1A against tubulin (1:1000) (Sigma-Aldrich Corp.), and their morphology examined using an Axiovert fluorescent microscope equipped with objectives 20x (dry) and 100x (oil immersion Neofluar) (Carl Zeiss, Germany).

Figure 5A:
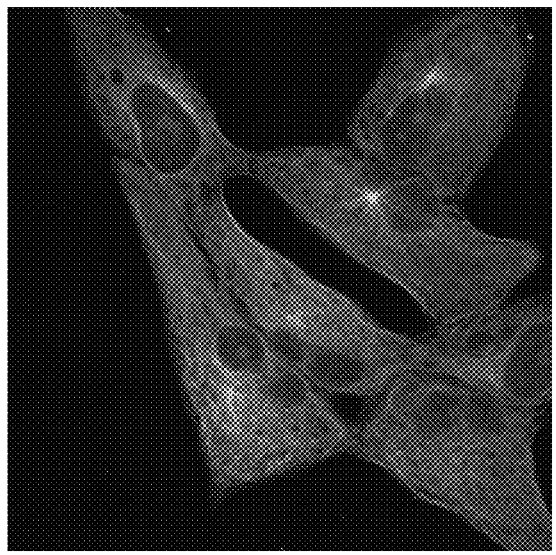
FIG. 5A is a representation of a micrograph showing RD cells treated with 1 mM NAC for 24 hours, and then stained with antibodies against actin (red) and tubulin (green); The same effect was observed with 100 μm Trolox.
Figure 5B:
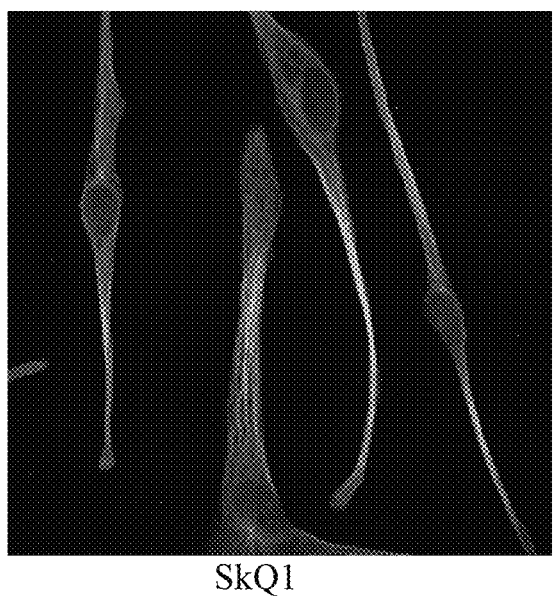
FIG. 5B is a representation of a micrograph showing RD cells treated with 20 nM SkQ1 for 24 hours and then stained with antibodies against actin (red) and tubulin (green)

As shown in FIG. 5, the morphology of the RD cells was similar to that of nondifferentiated myoblasts. Pretreatment with SkQ1, SkQR1, SkQB1, and SkQBP1 for 24 hours induced the formation of elongated cells resembling cells undergoing the early steps in myogenic differentiation.

Figure 6:
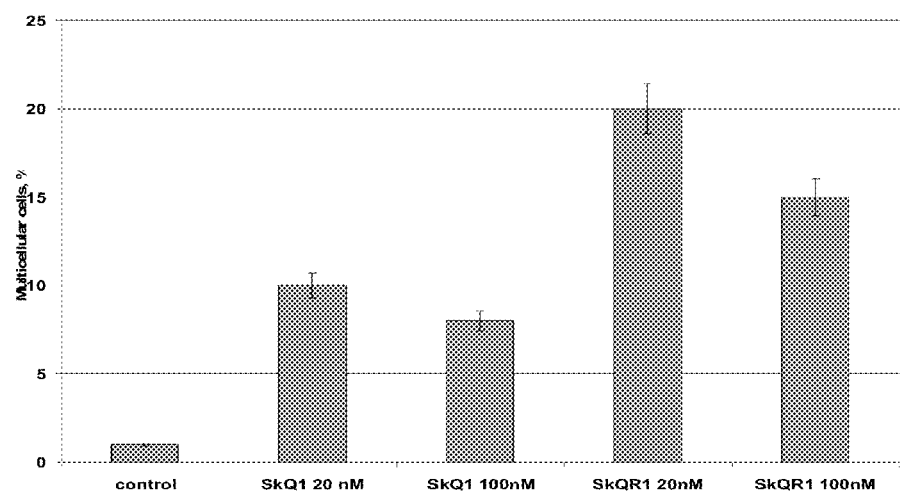
FIG. 6 is a graphic representation of the number of multinuclear cells in various RD cell samples treated with different concentrations of SkQ1 or SkQR1 for 8 days.

The major part of the treated RD cell population showed suppressed proliferation and cell death. Only about 4% of the cells remained attached to the surface at the 8th day of cultivation with nM SkQ1). However, the survival cell fraction was enriched in multinuclear cells similar to differentiated myotubes (FIG. 6).

To determine the viability of the cells, chromatine condensation and fragmentation was analyzed in similarly-treated cells (20 nM SkQ or 1 mM NAC or 100 mM Trolox for 24 hours and 1 μm FCCP one hour before SkQ1 where indicated) after staining with Hoechst 3342 (GenScript, Cat. No. L00309, performed according to manufacture manual http://www.genscript.com/tech_guide/TM0361.pdf). The cells were then examined using an Axiovert fluorescent microscope equipped with objectives 20× (dry) and 100× (oil immersion Neofluar) (Carl Zeiss).

Figure 7:
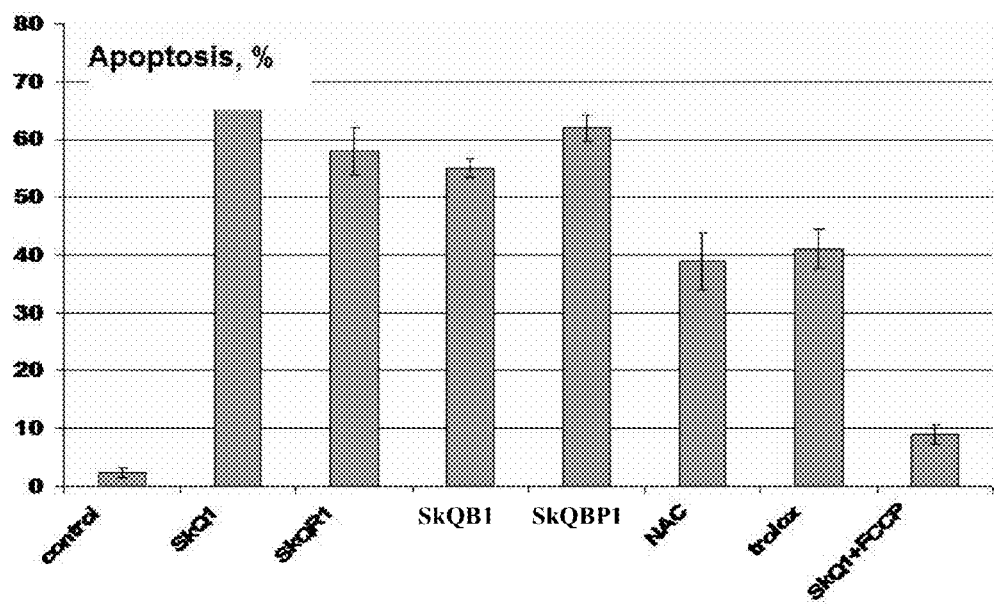
FIG. 7 is a graphic representation showing the induction of apoptosis in RD cells treated with various SkQs or with NAC or Trolox.

The results show that SkQs induced apoptosis in RD cells (FIG. 7). The protonophorous uncoupler FCCP dissipated the mitochondrial membrane potential, inhibited accumulation of SkQs in mitochondria, and prevented their pro-apoptotic action (FIG. 7). Non-targeted antioxidants NAC and Trolox also induced apoptosis in RD cells but only at much higher concentrations.

Further evidence of apoptosis was obtained by analysis of DNA content in the cellular population using flow cytometry. Cells were incubated with 0.05% ethanol was added (control) or with 20 nM SkQ1 for 24 hours, and then fixed and stained with propidium iodide (5 μM). They were then analyzed by flow cytometry using a FC-500 FACS (Beckman Coulter, Inc., Brea, Calif.).

Figure 8A:
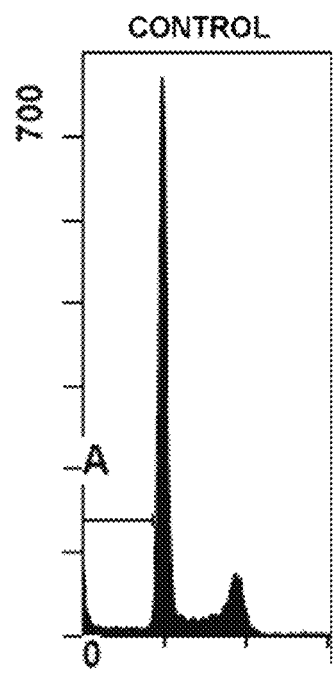
FIG. 8A is a representation of a histogram showing apoptotic bodies in a cell sample incubated without SkQ1 (0.05% ethanol was added (control) for 24 hours), and then fixed and stained with propidium iodide.
Figure 8B:
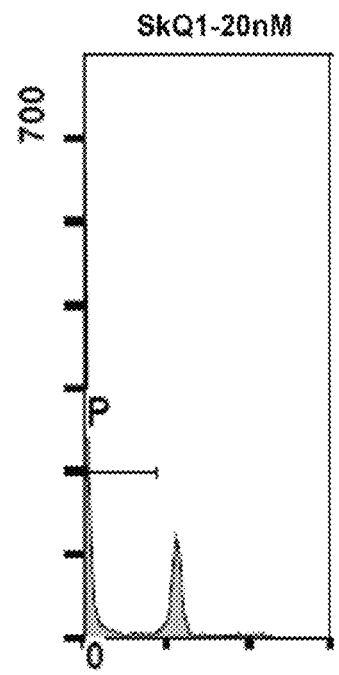
FIG. 8B is a representation of a histogram showing apoptotic bodies in a cell sample incubated with 20 nM SkQ1 for 24 hours, and fixed and stained with propidium iodide.

The sub-G1 peak of the histograms in FIGS. 8A and 8B indicate accumulation of apoptotic bodies in the cell culture. Cell death was prevented by the pan-caspase inhibitor zVAD-fmk, confirming the apoptotic mechanism of cell killing by the SkQs. The effectiveness of the various SkQs was similar.

The effect of SkQ on the level of ROS in cytoplasm was analyzed using the fluorescent ROS indicator DCF-DA (dichlorodihydrofluorescein diacetate, Invitrogen). Cells were treated with SkQR1 (20 mM) for 24 hours, incubated with the fluorescent ROS indicator DCF-DA, and then analyzed by flow cytometry FACs, FC-500 (Beckman Coulter, Inc., Brea, Calif.).

Figure 9:
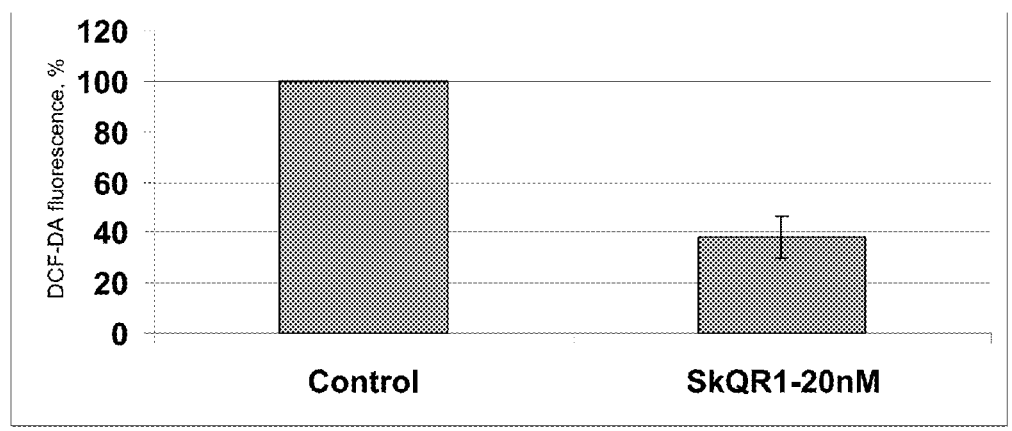
FIG. 9 is a graphic representation of the amount of reactive oxygen species (ROS) in RD cells treated with 20 nM SkQR1 or in control (untreated) RD cells incubated without SkQR1 (0.05% ethanol), stained with DCF-DA, and then analyzed by flow cytometry.

As shown in FIG. 9, a significant decrease of ROS in SkQ-treated cells was found. While not being held to any particular mechanism, the decrease in ROS level may have resulted in the inhibition of cell cycle progression in the RD cells. The mechanism of the induction of apoptosis may involve the aberrant cessation of the cell cycle. These data indicated that a high level of mitochondrial ROS is critical for survival of RD cells.

These experiments demonstrate that compounds of Structure (I) are useful for decreasing ROS, inducing apoptosis, and thus for treating cancers.

EQUIVALENTS

Those skilled in the art will recognize, or be able to ascertain, using no more than routine experimentation, numerous equivalents to the specific composition and procedures described herein. Such equivalents are considered to be within the scope of this invention, and are covered by the following claims.

The invention claimed is:

1. A method of treating a cancer in a mammal, wherein the cancer is selected from the group consisting of cervical carcinoma, fibrosarcoma, osteosarcoma, and rhabdomyosarcoma, comprising administering to the mammal a therapeutically effective amount of a pharmaceutical composition of a compound having the structural formula:

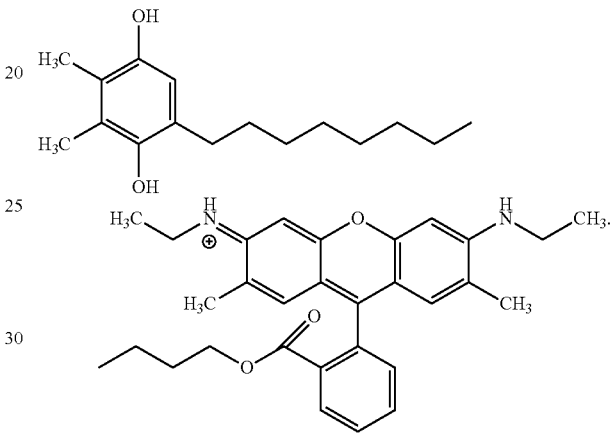

2. The method of claim 1, wherein the pharmaceutical composition is administered with another anti-cancer therapeutic.

3. The method of claim 1, wherein the pharmaceutical composition is a solution and is orally administered.

4. The method of claim 1, wherein the pharmaceutical composition is a solution and is parenterally administered.

5. The method of claim 1, wherein the pharmaceutical composition is an ointment, bandage, or film and is transdermally administered.

6. The method of claim 1, wherein the cancer is a Ras-related metastatic cancer.

7. A method of treating a cancer in a mammal, wherein the cancer is selected from the group consisting of fibrosarcoma, osteosarcoma, and rhabdomyosarcoma, comprising administering to the mammal a therapeutically effective amount of a pharmaceutical composition of one or more compound having a structural formula selected from:

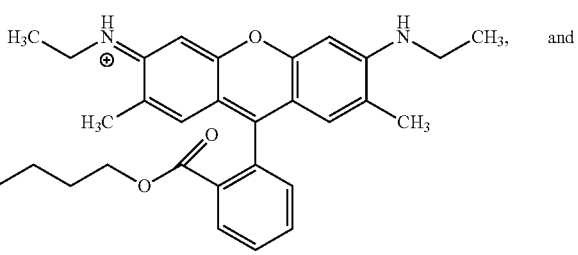

-continued

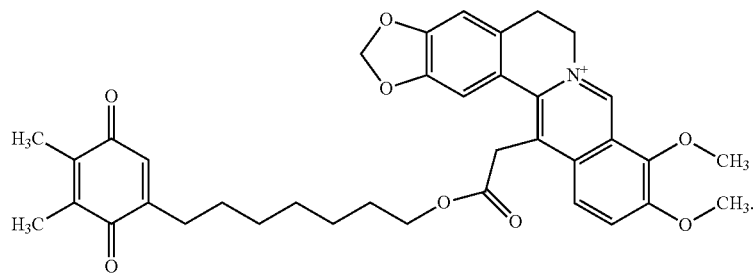

8. The method of claim 7, wherein the pharmaceutical composition is administered with another anti-cancer therapeutic.

9. The method of claim 7, wherein the pharmaceutical composition is a solution and is orally administered.

10. The method of claim 7, wherein the pharmaceutical composition is a solution and is parenterally administered.

11. The method of claim 7, wherein the pharmaceutical composition is an ointment, bandage, or film and is transdermally administered.

12. The method of claim 7, wherein the cancer is a Ras-related metastatic cancer.

13. A method of treating a cancer in a mammal, wherein the cancer is selected from the group consisting of osteosarcoma and rhabdomyosarcoma, comprising administering to the mammal a therapeutically effective amount of a pharmaceutical composition of one or more compound having a structural formula selected from

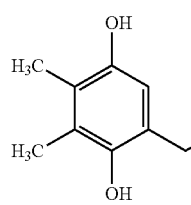 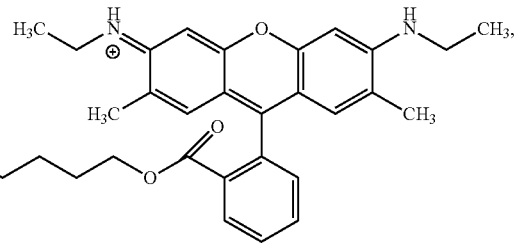

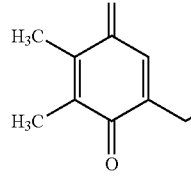 and

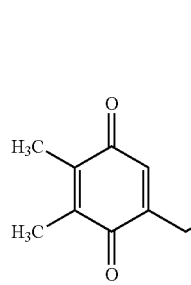 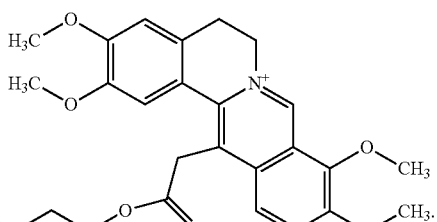

14. The method of claim 13, wherein the pharmaceutical composition is administered with another anti-cancer therapeutic.

15. The method of claim 13, wherein the pharmaceutical composition is a solution and is orally administered.

16. The method of claim 13, wherein the pharmaceutical composition is a solution and is parenterally administered.

17. The method of claim 13, wherein the pharmaceutical composition is an ointment, bandage, or film and is transdermally administered.

18. The method of claim 13, wherein the cancer is a Ras-related metastatic cancer.

* * * * *